United States Patent [19]

O'Leary

[11] 4,343,315
[45] Aug. 10, 1982

[54] METHOD OF AND APPARATUS FOR MEASURING THE PHYSICAL CONDITION OF A PERSON

[75] Inventor: John B. O'Leary, Minnetonka, Minn.

[73] Assignee: Grey-Mac Fitness, Ltd., Minneapolis, Minn.

[21] Appl. No.: 161,574

[22] Filed: Jun. 20, 1980

[51] Int. Cl.³ ............................ A61B 5/02; A61B 5/00
[52] U.S. Cl. .................................... 128/689; 128/695
[58] Field of Search ............... 128/707, 666, 689, 903, 128/710, 695; 434/255, 247; 272/70, 100

[56] References Cited

U.S. PATENT DOCUMENTS

| | | | |
|---|---|---|---|
| 1,435,660 | 11/1922 | Ragerson . | |
| 2,457,968 | 1/1949 | Allen et al. | 434/255 X |
| 3,492,582 | 1/1970 | Heinwood | 434/255 X |
| 3,518,985 | 7/1970 | Quinton | 272/69 X |
| 3,675,640 | 7/1972 | Gatts | 272/69 X |
| 3,846,704 | 11/1974 | Bessette | 434/255 X |
| 4,028,693 | 6/1977 | Kuntz | 434/255 X |
| 4,038,976 | 8/1977 | Hardy et al. | 128/903 X |
| 4,181,134 | 1/1980 | Mason et al. | 128/689 |
| 4,202,350 | 5/1980 | Walton | 128/690 |

FOREIGN PATENT DOCUMENTS

| | | | |
|---|---|---|---|
| 718131 | 11/1954 | United Kingdom | 128/903 |
| 665888 | 5/1979 | U.S.S.R. | 128/707 |

OTHER PUBLICATIONS

"Metretel Biomedical Telemetry Systems", Avionics Research Products Corp., Los Angeles, Calif.
Hoodless, D. J., et al., "A Portable Physiological Data Recording/Decoding System," J. Biomed. Engrg., vol. 2, No. 3, Jul. 1980, pp. 193–196.
Bassen et al., Clinical Science and Molecular Medicine, vol. 51, 1976, pp. 609–612.

Primary Examiner—Kyle L. Howell
Assistant Examiner—J. C. Hanley
Attorney, Agent, or Firm—Kinney, Lange, Braddock, Westman & Fairbairn

[57] ABSTRACT

The invention relates to an apparatus for testing the physical condition of a person and a method for using the apparatus. The apparatus comprises a portable heart monitor for attachment to a person and a plurality of circular paths positioned for sequential use by the person in order of increasing size. Marked on the circles are means indicating a given fractional part of the circle which is to be covered in a measured number of seconds. Means are provided to indicate the elapsing of the measured number of seconds. Additionally provided are means timing the elapse of a set period of time for the person to sequentially walk over each circle.

The method comprises the steps of operably attaching the portable heart rate monitor to a person and having the person sequentially walk over a plurality of predetermined circular paths for a set period of time for each circle at a speed defined by requiring the walker to make a given fractional revolution per measured number of seconds, such that the sequential plurality of circles have an increase in size by an amount sufficient to give a step function increase in the speed of walking. The portable heart rate monitor continuously records for evaluation heart rate of the person during the walk.

In a preferred embodiment, an alarm is provided as a safety precaution to signal the observation of an abnormal heart rate. It is contemplated that a plurality of persons can employ the apparatus and method of this invention simultaneously to permit the testing of the physical condition of a group of people in an efficient manner.

11 Claims, 3 Drawing Figures

3 mph
3.5 mph
4 mph
4.5 mph

METHOD OF AND APPARATUS FOR MEASURING THE PHYSICAL CONDITION OF A PERSON

BACKGROUND OF THE INVENTION

There is a substantial need for a simple, accurate field method for determining physical fitness. Fitness testing by single stage exercises and manual recording of pulse rate after exercise have not correlated well with the multi-stage treadmill and bicycle ergometer methods used in physiological reserach laboratories. The criteria of such a method is simplicity, accuracy and reproducibility. All three of these requirements are important if a true evaluation of physical fitness is to be achieved. It is necessary to provide a cost effective method for evaluating school, community and military fitness programs and it is also desirable to provide a less expensive alternative to traditional exercise testing methods for following individual exercise and cardiac rehabilitation therapy.

There has been no simple accurate technique for estimating an individual's physical fitness level. Questionnaire and interview techniques are inaccurate because people differ in skills and habits, and the same type of work or play may involve vastly different energy expenditures. There is clearly a need for a simple but accurate test of fitness levels, particularly in North America where studies have indicated that fitness levels among North Americans are lower than among genetically similar populations in Europe.

Most studies on the effective exercise on cardiovascular systems have been concerned with th pulse rate and blood pressure response to exertion. Investigators have shown that subjects exhibit a gradually increasing heart rate when work loads are successively increased on a treadmill or on a bicycle ergometer. As the work load increases, the more physically fit individuals will in general show a relatively slower increase in pulse rate, although with actual athletic performance of elite athletes, the opposite may occur. It has also been noted that more physically fit athletes will not only be able to sustain a higher heat rate but will also have their heart rate return to normal more rapidly after stopping activity.

Three basic methods of fitness testing have emerged as somewhat practical for predicting athletic performance. The simplest method is the step test. This test has been described as being an arbitrary criterion based upon test endurance, work accomplished and heart rate. It is not highly reproducible and does not correlate between individuals. The more complex, but also more reliable methods are available speed treadmill testing and bicycle ergometry. Both of these latter methods are good predictors when maximum oxygen consumption is used as an index of cardiovascular efficiency. Because the heart rate response to graded exercise loads correlates well with maximum oxygen intake, this finding has simplified testing and these tests have proven useful in separating groups of athletes from non-athletes. Heart rate monitoring of subjects at graded work loads have also been valuable for prescribing exercise regimens in cardiac rehabilitation. While variable speed treadmill testing is quite reliable, such equipment is very expensive and bulky, making it difficult to move.

Several studies have suggested that the heart rate is a linear function of work speed and as such is somewhat independent of body weight at normal working speeds.

As far as applicant is presently aware, very few patents are even remotely related to the problem of evaluating physical fitness while the patient is exercising. U.s. Pat. No. 1,435,660 discloses an educational appliance which has a sound recording and a visual illustration representing the various movements described in the record. British Pat. No. 718,131 describes a means for detecting and recording electrical changes in the body including, apparently, heart pulse rate. The patent describes various electrodes attached to the body along with a transmitter and receiver for recording and display, which make it possible to measure various physical factors, such as heart pulse rate, while the patient is moving about or is in "situations of particular stress". U.S. Pat. No. 3,846,704 discloses an apparatus for evaluating an athletic performance, but it is primarily concerned with the relationship of the individual athlete with respect to a predetermined performance, such as a world record performance, which the athlete can compare his efforts to during his performance of his event. The apparatus has a programmed central control for sequentially energizing various lights responsive to the programmed optimum performance and the athlete judges his performance relative to the occurrence of various flashing lights as he passes various points on his event. The runner can have his heart pulse rate continuously monitored but the purpose of this is to compare the pulse rate with the optimum one desired for an athlete and to indicate when the heart beat rate departs from a predetermined rate.

SUMMARY OF THE INVENTION

The method and apparatus of the present invention are concerned with measuring the physical fitness of a person in a manner capable of meeting the criteria of simplicity, accuracy and reproducibility. The method is a cost effective method for evaluating school, community and military fitness programs and provides a less expensive alternative to traditional exercise testing methods for monitoring individual exercise and cardiac rehabilitation therapy.

The apparatus, according to the present invention for testing the physical condition of a person, comprises a portable heart rate monitor for attachment to the person and a closed curved path positioned for sequential use by the person in order of increasing size. Means marking a predetermined portion of the path to be covered in a measured number of seconds are placed on the paths and means indicating the elapsing of the measured amount of time is provided. Finally, timing means measuring the occurrence of a set period of time for said person to sequentially walk over each path is provided.

In a preferred embodiment, the paths are concentric circles so that the person walking the circles can step laterally to the next largest circle after each set period of time. Other configurations such as tangent or adjacent circles are also useful but require more space. The heart rate monitor preferably is adapted to provide an alarm upon observing an abnormal heart rate to prevent adverse effects during testing.

To coordinate the efforts of the walker on the paths, specific means indicating the elapsing of the measured number of seconds are provided. These comprise a signal emitting device for emitting a signal after each preset interval. The walker coordinates his pace so that he passes the predetermined portion of the path each time the measured number of seconds are indicated to have elapsed. This predetermined portion may be any portion of the path including the complete path. In a preferred form, the portion is one-half of the path.

The signal emitting device may be a device which emits a sound after a predetermined number of seconds. In a preferred embodiment, the signal emitting device includes an electrical current source, a timing circuit, and a sound generating means adapted to receive current at intervals set by the timing circuit.

It is preferred that the increase in rate caused by changing to larger paths be a step function. Preferably the step function rate increase will be at least one-fourth mile per hour for each increase in path size. Normally, the rate increases from about two miles per hour to about six miles per hour. In a preferred embodiment, a suitable program for measuring the physical condition of a person includes a rate increase of from about three miles per hour to about 4.5 miles per hour in one-half mile per hour step functions. The travel at each speed, thereby the travel at each circle, is maintained for a sufficient time to allow the exercise to increase the heart rate to a new steady state. Since the heart normally adjusts to minor increases in exercise within one to two minutes, three minutes is a safe measure to achieve a steady state heart rate.

BRIEF DESCRIPTION OF THE DRAWINGS

For a more complete understanding of the invention, reference is hereby made to the drawings, in which.

DESCRIPTION OF THE PREFERRED EMBODIMENT

Figure 1:
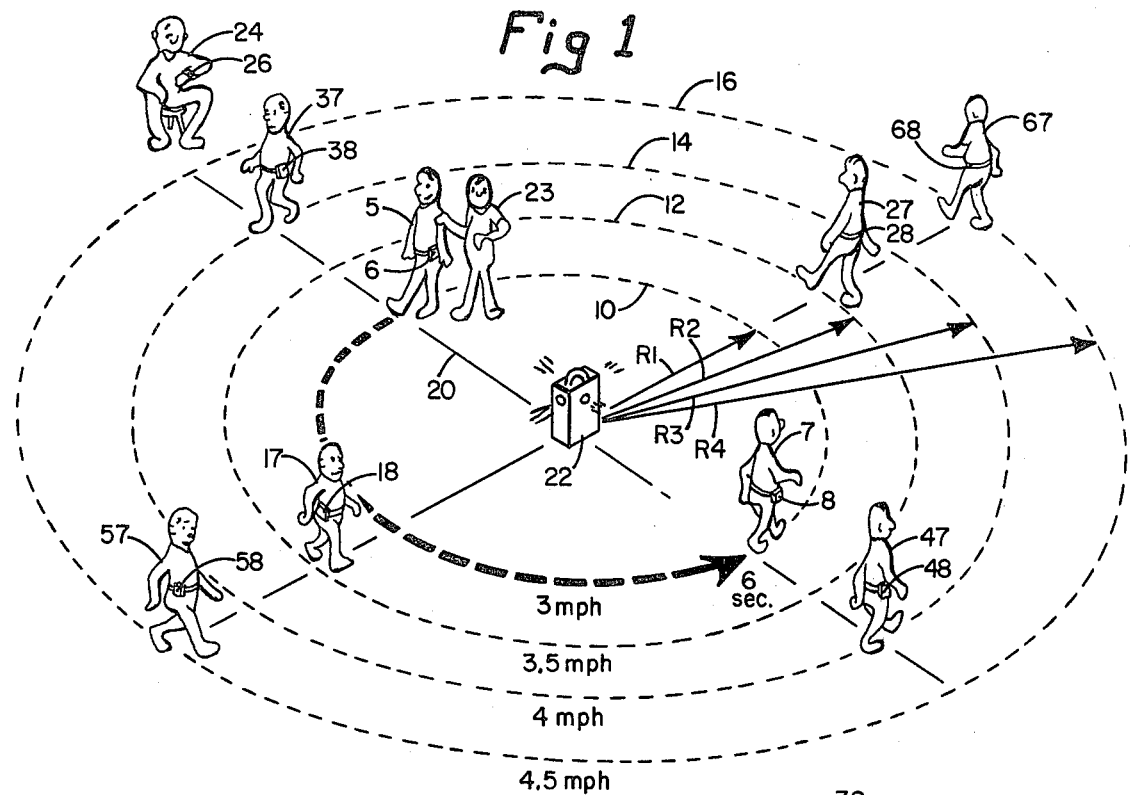
FIG. 1 is a schematic diagram illustrating the operation of the preferred embodiment of the present invention.

As shown in FIG. 1, a plurality of individuals 5, 7, 17, 27, 37, 47, 57 and 67 are present for testing their physical condition. One each of a plurality of heart rate monitors 6, 8, 18, 28, 38, 48, 58 and 68 is attached to each of the individuals 5, 7, 17, 27, 37, 47, 57 and 67. In the case of monitors 28 and 68, only the supporting straps are shown. One particularly suitable heart rate monitoring device is the Holter Model 445, two channel Electrocardiocorder. In the embodiment, the persons were instructed to commence walking on a plurality of predetermined circular paths 10, 12, 14 and 16 for a set period of time starting at start line 20. A signal emitting device 22 was conveniently placed at the center of the circles and emitted a signal after the end of a predetermined number of seconds, such as 6 seconds.

Each person was instructed by a starter 23 to begin walking at the sound of the signal emitting device and to go halfway around the path by crossing the center line 20 each time the device emitted the sound. Observer 24, using watch 26, was able to coordinate the efforts of the individuals so that after a set period of time, nominally three minutes, the individuals were required to increase their path being traveled from circle 10 to circle 12, then after another set period, to circle 14, and so on through circle 16. Since the signal emitting device 22 maintained a constant number of seconds between sounds being emitted, and since the persons 5, 7, 17, 27, 37, 47, 57 and 67 were required to make one-half revolution each time a sound was emitted, the persons were required to travel at a faster speed on each circular path. Each individual was subjected to a step function increase in physical effort while carrying the portable heart rate monitoring device 8.

It will be noted that there are two persons on track 10, 2 on track 12, 2 on track 14 and 2 on track 16. The people being tested are controlled by the starter 23 and the observer 24 in such a manner that no two people are abreast of each other in adjoining tracks. Thus, individuals 7 and 47, while abreast of each other, are spaced apart by twice the distance between tracks. The same is true of all of the individuals being tested. This may be accomplished either by the times at which people are started running or by the time at which they switch from one track to another. It will thus be seen that with the 4 tracks, 8 people are being tested without any two being closely adjacent to each other.

Figure 2:
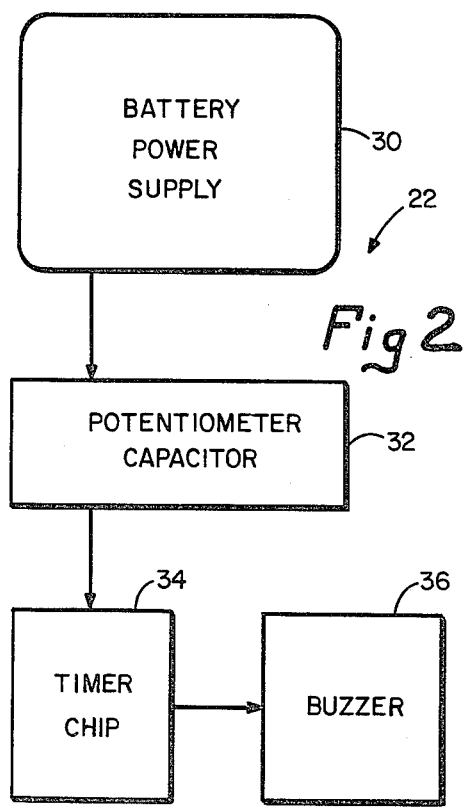
FIG. 2 is a block diagram of the timer used in FIG. 1.

One simple form of signal emitting device 22 is shown schematically in FIG. 2. A battery power supply 30 provides a source of power for a timer 34 which can be the well known 555 timing chip. The timing period of the timer 34 is controlled by a potentiometer capacitor combination which can be adjusted to vary the timing period. At the end of each timing period, the timer 34 causes actuation of a buzzer 36.

Figure 3:
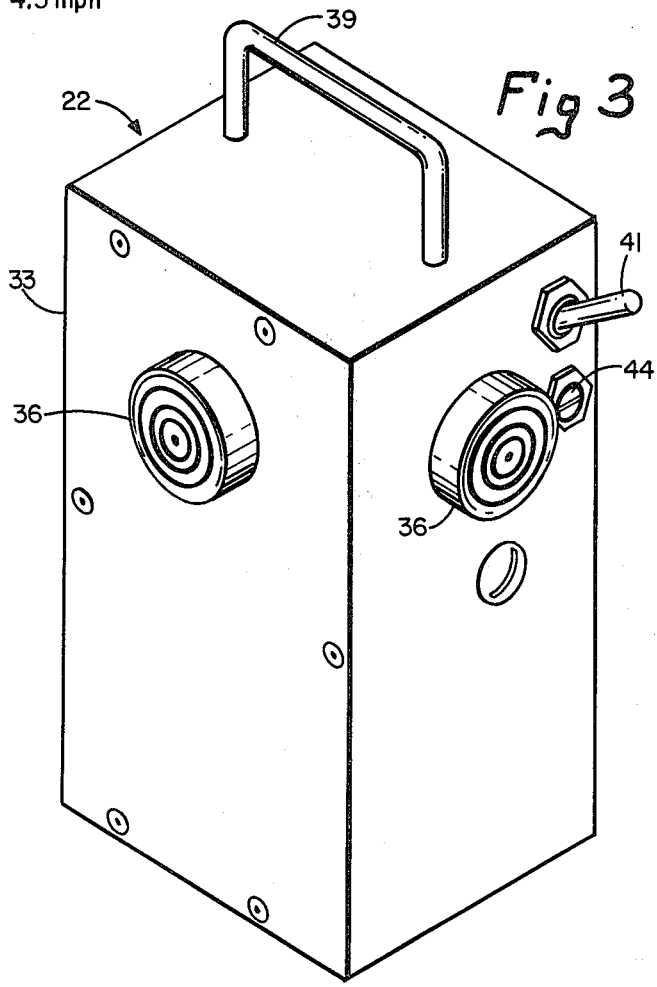
FIG. 3 is a perspective view of the timer.

In FIG. 3, I have shown the physical form which the timing apparatus 22 of FIG. 2 may take. It will be noted that there is a case 33 having a handle 39 secured thereto for carrying the case. Secured within the case and extending through the wall of the case are four buzzers 36, only two of which are shown in the drawing. The device is provided with a switch for disconnecting the power supply from the timer 34 and the buzzers 36. The switch is in the form of a toggle switch having a handle 41. The potentiometer or capacitor of the potentiometer capacitor unit 32 may be adjusted by any sort of suitable means such as a shaft having a slotted head 44 which is accessible from outside of the case 33. In use, the timer unit 22 is placed in the center of the circles as shown in FIG. 1 by placing the case 33 on the floor at that point.

To demonstrate the efficiencies of the present invention, a group of individuals were subjected to the method of the present invention using the apparatus described herein. As a safety precaution, physical examinations were made of each of the subjects and smoking and meals were prohibited for one hour prior to testing. Each subject was fitted with a Holter Model 445, two channel electrocardiocorder and a timing device as described herein was employed to emit a short beep or sound at six second intervals plus or minus 0.01 seconds. The concentric circles and the bisecting straight line were constructed from tape. The radius of the circles were measured so that a subject walked on a taped circle with a radius $R_1$ of 8.4 ft. and completed a lap every 12 seconds; that is, he crossed the center tape 20 every six second beep. This rate computes to three miles per hour. A second circle had a radius $R_2$ of 9.8 ft. to give a walking speed of 3.5 miles per hour. An 11 ft., 2 inch radius $R_3$ yielded a 4.0 mile per hour speed and a 12.6 radius $R_4$ equals a walking speed of 4.5 miles per hour. The step function increase can easily be handled by most subjects. Obviously, slower walking or faster running speeds can be employed, depending upon the age and condition of the people being tested.

Subjects were instructed to start walking at the point marked on the bisecting line on the inner circle at the sound of a beep. The event marker on the Holter monitor was pressed at the time the subject started to walk. Subjects were instructed to walk on the taped circle until told to switch to a wider circle, which occurred every three minutes. Upon completion of all four circles, totaling an elapsed time of 12 minutes, the event marker on the Holter monitor was again pressed and the Holter monitor disconnected to be used on the next subject. By the use of eight Holter monitors, eight subjects can be controlled at one time by the same observer.

In the test, no subjects had difficulty in adjusting walking speeds to the sound of the timing device after the first 12 to 24 seconds. One subject had to run occasionally at the 4.5 mile per hour walking speed. No subject developed chest pain or palpitations during the field test. When mean average heart rates were calculated and plotted in relation to the four walking speeds, the relationship appeared essentially linear.

Since it is known that a person in better physical condition will have a slower increase in heart rate for a given amount of exercise, minimum standards can be prepared for particular age and fitness levels and large groups of people can be tested to see how their fitness levels compare to the normal or desirable level of heart rate increase. Upon acquisition of sufficient data, an experienced test group can probably test up to 100 subjects per hour in a normal size gymnasium. Thus, a method has been defined for measuring the physical condition of a person which has met the criteria of simplicity, accuracy and reproducibility.

The Holter monitor is preferably equipped, as indicated above, with any conventional means for indicating when the heart rate is abnormal. Such an alarm means may be equipped with means for transmitting a warning signal to the observer 24 in the event of such an abnormal heart rate being sensed. Equipment of this type is well known and in use in intensive coronary care units.

While a specific embodiment of the invention has been described for purposes of illustration, it is to be understood that the scope of the invention is limited solely by the appended claims.

What is claimed is:

1. A method of simultaneously testing the physical condition of a plurality of persons, comprising the steps of:
providing a plurality of adjacent paths of progressively different lengths, the length of the longest path being at least twenty-five percent greater than the length of the shortest path,
having each person sequentially walk over each path in said plurality of paths in the same set period of time for each path, at a speed defined by requiring each walker to cover the length of each path in the same predetermined time interval, and after the set period of time, having each person move to an adjacent path of greater length, said persons moving progressively from the shortest path to paths of progressively increasing length such that the walking speed is progressively increased, and
continuously observing the heart rate of each person.

2. The method of claim 1 wherein the persons walk around circular paths.

3. The method of claim 2 wherein the persons walk sequentially around concentric circular paths.

4. The method of claim 1 wherein said speed is defined by requiring each person to cover one-half of each path in a measured number of seconds.

5. The method of claim 4 wherein the measured number of seconds is determined by a signal emitting device for emitting a signal at a preset interval.

6. The method of claim 5, wherein said signal emitting device emits a sound every predetermined number of seconds.

7. The method of claim 1 wherein each such increase in walking speed is at least one-quarter mile per hour.

8. The method of claim 1 wherein the speed increases from about two miles per hour to about six miles per hour as the person moves from one path to the next path.

9. The method of claim 1 wherein the speed increases from three miles per hour to 4.5 miles per hour in one-half mile per hour step functions as the person moves from the shortest path to the path of greatest lengths.

10. The method of claim 1 wherein the spaced paths are predetermined closed curved paths.

11. The method of claim 1 in which a portable heart rate monitor is attached to each person and the heart rate of each person is continuously recorded by such monitors.

* * * * *